United States Patent [19]

Brackenridge

[11] Patent Number: 4,960,962

[45] Date of Patent: Oct. 2, 1990

[54] SELECTIVE DEHYDROBROMINATION

[75] Inventor: David R. Brackenridge, Baton Rouge, La.

[73] Assignee: Ethyl Corporation, Richmond, Va.

[21] Appl. No.: 381,829

[22] Filed: Jul. 19, 1989

[51] Int. Cl.$^5$ .................. C07C 17/24; C07C 17/34
[52] U.S. Cl. ........................... 570/200; 570/204; 570/220
[58] Field of Search .................. 570/200, 204, 220

[56]  References Cited

U.S. PATENT DOCUMENTS

| | | | |
|---|---|---|---|
| 3,560,580 | 2/1971 | Burk | 570/200 |
| 3,737,469 | 6/1973 | Berger et al. | 260/650 |
| 3,867,468 | 2/1975 | Vofsi et al. | 260/650 |
| 3,966,831 | 6/1976 | Levy et al. | 260/650 |
| 3,980,722 | 9/1976 | Cohen et al. | 260/650 |
| 4,292,453 | 9/1981 | Daren et al. | 570/193 |
| 4,423,262 | 12/1983 | Jackisch | 570/193 |
| 4,633,026 | 12/1986 | Kolich | 570/200 |

FOREIGN PATENT DOCUMENTS 499681 2/1954 Canada .................. 570/204

OTHER PUBLICATIONS

Daren et al., *British Polymer Journal*, 1975, vol. 7, pp. 247-261.

*Primary Examiner*—Werren B. Lone
*Attorney, Agent, or Firm*—John F. Sieberth; David E. LaRose

[57]  ABSTRACT ar-Bromoaromatics having an alkenyl side chain on the aromatic nucleus are formed by feeding a beta-bromoalkyl-ar-bromoaromatic compound, together with a substantial excess of water, into a thermal dehydrobromination zone held at or above 475° C., and maintaining a very short residence time (5 seconds or less) in the dehydrobromination zone. Very little extraneous coproducts are formed. For example dibromostyrene was produced by co-feeding bromoethyldibromobenzene (BEDB) and excess amounts of water (using nitrogen as a carrier gas) into a Vycor tube packed with glass beads at 500° C. By suitable controlling residence times, the amount of undesired coproducts formed was kept below 1.5 G. C. area %, and the percentage of BEDB conversion was in the range of 84.1% up to 99.1%.

20 Claims, No Drawings

SELECTIVE DEHYDROBROMINATION

FIELD

This invention relates to and has as its principal object selective dehydrobromination of alkylaromatics having as ring substituents at least one dehydrobrominatable bromoalkyl group and at least one bromine atom.

BACKGROUND

Thermal dehydrobromination of beta-bromoethyl bromoaromatic compounds tends to result in the formation of excessive quantities of unwanted by-products. For example when bromoethyldibromobenzene was passed through a vertical hot tube reactor packed with glass beads at 350-500° C., dehydrobromination to form ar-dibromostyrene was accomplished, but significant amounts (ca. 5%) of extraneous brominated ethylbenzene coproducts and several unknown coproducts (ca. 1%) were formed. Use of several solid catalysts in the packed column in lieu of the glass beads resulted in an increase in the quantities of these extraneous coproducts.

Levy et al U.S. Pat. No. 3,966,831 describes a process for the production of mono-, di-, and/or tribromostyrene by reacting beta-bromoethyl mono-, di-, and/or tribromobenzene at a temperature between 280 and 470° C. in the presence of a free radical source and either a lower alkanol or water. As shown by Examples 6 and 7 of the patent, in reactions conducted at 360° C. elimination of the the peroxide or hydroperoxide free radical source resulted in extremely low conversions to the bromostyrene (30%).

THE INVENTION

In one of its embodiments this invention provides a process for producing ar-bromostyrenes from beta-bromoethyl bromobenzenes in high yield and selectivity without use of a catalyst or free radical source. In the process the bromine atom is selectively removed from the bromoethyl group as hydrogen bromide, but the ring-substituted bromine atom(s) remain(s) intact. Moreover, the hydrogen bromide released in the process is prevented from reacting to any undesirable extent with the olefinic side chain formed as a result of the dehydrobromination of the bromoethyl group. The hydrogen bromide co-product can be readily recovered for use in other synthesis processes.

In accordance with this invention, a beta-bromoalkyl ar-bromoaromatic compound together with a substantial molar excess of water is fed into and rapidly passed through a thermal dehydrobromination zone maintained at a temperature of least 475° C. whereby the bromoalkyl side chain is converted by dehydrobromination to an alkenyl group and very little extraneous coproducts are formed. The residence time for the reactant and reaction product in the high temperature dehydrobromination zone should be less than about 5 seconds, preferably 2 seconds or less, and for best results this rapid reaction is conducted in the vapor phase in a packed column containing glass beads or other solid inert packing material. Other than a carrier gas (air, nitrogen, argon, or the like) no other substances are fed into the reactor. The interior reaction zone of the reactor itself should be fabricated from inert high-temperature resistant materials such as Vycor glass, tantalum, or the like.

If desired, the process can be applied to monobromoalkylbromobenzenes in which a dehydrobrominatable bromoalkyl group (e.g., 2-bromoethyl, 2-bromopropyl, 2-bromoisopropyl, 2-bromobutyl, etc.) is bonded to a benzene ring which also has bonded thereto from 1 to 5 bromine atoms and from 0 to 4 hydrocarbyl groups (e.g., alkyl, aryl, cycloalkyl, aralkyl, cycloalkylalkyl, etc.). A few illustrative compounds of this type include the 2-bromoethylbromobenzenes, the 2-bromoethyldibromobenzenes, the 2-bromoethyltribromobenzenes, the 2-bromoethyltetrabromobenzenes, 2-bromoethylpentabromobenzene, the 2-bromoethyl-ar-bromotoluenes, the 2-bromoethyldi-ar-bromotoluenes, the 2-bromoethyl-tri-arbromotoluenes, the 2-bromoethyl-tetra-ar-bromotoluenes, the 2-bromoethyltribromoxylenes, the 2-bromopropyltribromobenzenes, the 2-bromopropyltetrabromobenzenes, 2-bromopropylpentabromobenzene, the 2-bromoisopropylbromobenzenes, the 2-bromoisopropyldibromobenzenes, the 2-bromoisopropyltribromobenzenes, the 2-bromoisopropyltetrabromobenzenes, 2-bromoisopropylpentabromobenzene, and the like. The preferred reactants are 2-bromoethyl mono-, di- and tribromobenzenes, either singly or in any mixture of two or more of these compounds.

Preferably, the reaction is conducted at a temperature in the range of about 475 to about 550° C., and more preferably in the range of about 490 to about 520° C. Excellent results have been achieved at 500° C.

The amount of water introduced in the dehydrobromination zone along with the bromoalkyl bromoaromatic reactant is not critical provided there are at least about 8 mols of water, and preferably at least about 15 mols of water per mol of hydrogen bromide theoretically released from the bromoalkyl group undergoing dehydrobromination in the dehydrobromination zone. The water may be introduced in the form of liquid water or as a preformed vapor (steam). The water and the bromoalkyl bromoaromatic may be pre-mixed before introduction into the dehydrobromination zone or they may be introduced into the zone separately but concurrently.

In a preferred embodiment of this invention the effluent from the dehydrobromination zone is rapidly chilled as it leaves the dehydrobromination zone to prevent or at least suppress the extent to which the alkenyl bromoaromatic product (e.g., ar-bromostyrene) is polymerized thermally. To illustrate, in a run conducted as in Example 4 hereinafter, the amount of polymer formation was kept to less than 0.1% by quick-freezing the effluent from 500° C. to −30° C. over a distance of three inches at the flow rates shown in Example 4. In another preferred embodiment of this invention wherein it is desired to form a polymer of the alkenyl bromoaromatic dehydrobromination product, the hot effluent from the dehydrobromination zone is fed directly into a polymerization reactor under conditions conducive to polymer formation.

The alkenyl bromoaromatics producible by the process of this invention are useful as flame retardants for polymers such as polyolefins, ABS, polystyrenes, polyesters, polyurethanes, polyphenylene oxides, blends of polyphenylene oxides with polystyrenes (which may be rubber free or rubber modified), and the like. Likewise, the alkenyl bromoaromatic products may be oligomerized to form materials useful as cutting oil additives or extreme pressure additives. When polymerized to form high polymers, the polymeric products are useful as flame retardants for polymers and plastics, and as molding resins for the production of films, fibers, coated and laminated articles, and the like.

The practice and advantages achievable by the practice of this invention were illustrated by a group of experiments described in the following examples.

EXAMPLES 1-4

In these experiments, bromoethyldibromobenzene ("BEDB") was converted to dibromostyrene ("DBS") in a hot Vycor tube packed with glass bead media at 500° C. by co-feeding the DBS with excess amounts of water using nitrogen as the carrier gas. The effluent was subjected to gas chromatographic analysis to determine the amounts (G. C. area percentages) of DBS and BEDB (BEDB of course being suitable for recycle), as well as ethyldibromobenzene ("EDBB") and unknown coproducts ("X"). The results of these experiments are summarized in the following table.

| Ex. No. | Gas Velocity, cc/min | | | Estimated Residence Time, Seconds | % BEDB Conv. | G.C. Area % | | | |
|---|---|---|---|---|---|---|---|---|---|
| | BEDB | H20 | N2 | | | DBS | BEDB | EDBB | X |
| 1 | 470 | 3154 | 195 | 0.22 | 84.1 | 78.5 | 20.1 | 0.3 | 1.1 |
| 2 | 470 | 1967 | 195 | 0.32 | 93.3 | 89.6 | 9.0 | 0.7 | 0.7 |
| 3 | 216 | 1967 | 195 | 0.35 | 94.0 | 90.7 | 8.2 | 0.6 | 0.5 |
| 4 | 52 | 457 | 195 | 1.19 | 99.1 | 97.6 | 1.3 | 0.7 | 0.4 |

It can be seen from the data in the above table that in each run the amount of undesired coproducts (EDBB and X) was below 1.5 G. C. area %, and that by suitably increasing residence time it was possible to raise the percentage of BEDB conversion from 84.1% up to 99.1%.

As noted above, it is a simple matter to recycle unreacted bromoalkyl bromoaromatic compound into the dehydrobromination zone should this be found desirable or advantageous in any given situation.

This invention is susceptible to considerable variation within the spirit and scope of the ensuing claims, and thus this invention is not intended to be limited by the specific exemplifications hereinbefore set forth.

What is claimed is:

1. A process which comprises (i) feeding into a thermal dehydrobromination zone maintained at a temperature of least 475° C., a mixture consisting of (a) one or more 2-bromoalkyl ar-bromoaromatic compounds, (b) a substantial excess of water, and (c) optionally a carrier gas, whereby the bromoalkyl side chain is converted by dehydrobromination to an alkenyl group, and (ii) maintaining the residence time for the reactant(s) and reaction products in such high temperature dehydrobromination zone at less than about 5 seconds, so that one or more ar-bromoaromatic compounds having an alkenyl side chain are produced.

2. A process of claim 1 wherein said mixture is preformed before it is fed into the dehydrobromination zone.

3. A process of claim 1 wherein said mixture is formed in situ by introducing at least components (a) and (b) separately but concurrently into the dehydrobromination zone.

4. A process of claim 1 wherein said residence time is 2 seconds or less.

5. A process of claim 1 wherein the dehydrobromination reaction is conducted in the vapor phase in a packed column containing glass beads or other solid inert packing material.

6. A process of claim 1 wherein said mixture includes a carrier gas.

7. A process of claim 6 wherein the carrier gas is predominantly nitrogen.

8. A process of claim 1 wherein the temperature of the dehydrobromination zone is maintained within the range of about 490 to about 520° C.

9. A process of claim 1 wherein the feed to the dehydrobromination zone includes at least about 8 mols of water per mol of hydrogen bromide theoretically released from the bromoalkyl group undergoing dehydrobromination in the dehydrobromination zone.

10. A process of claim 1 wherein the effluent from the dehydrobromination zone is rapidly chilled as it leaves the dehydrobromination zone to prevent or at least suppress the extent to which the alkenyl bromoaromatic product is polymerized thermally.

11. A process of claim 1 wherein the bromoalkyl bromoaromatic compound fed to the dehydrobromination zone is a 2-bromoethyl-ar-bromoaromatic compound.

12. A process for producing ar-monobromostyrene, ar-dibromostyrene, or ar-tribromostyrene, or any mixture of any two or all three of these, which comprises (i) feeding into a thermal dehydrobromination zone maintained at a temperature in the range of about 490 to about 520° C., a mixture consisting of (a) one or more 2-bromoethyl-ar-bromobenzenes having up to 3 bromine atoms on the ring, (b) at least 8 mols of water per mol of component (a), and (c) an inert carrier gas, whereby the bromoethyl side chain is converted by dehydrobromination to a vinyl group, and (ii) maintaining the residence time for the reactant(s) and reaction products in such high temperature dehydrobromination zone at less than about 5 seconds such that the amount of organic co-products of the reaction excluding 2-bromoethyl-ar-bromobenzene(s) fed into said zone is kept below about 1.5%.

13. A process of claim 12 wherein the 2-bromoethyl-ar-bromobenzene fed to the dehydrobromination zone is predominantly 2-bromoethyl-ar-dibromobenzene.

14. A process of claim 12 wherein the temperature of the dehydrobromination zone is maintained at about 500° C., and wherein the residence time in the dehydrobromination zone is 2 seconds or less.

15. A process of claim 12 wherein the dehydrobromination reaction is conducted in the vapor phase in a packed column containing glass beads or other solid inert packing material.

16. A process of claim 12 wherein the carrier gas is predominantly nitrogen.

17. A process of claim 12 wherein said mixture includes at least about 15 mols of water per mol of component (a).

18. A process of claim 12 wherein the effluent from the dehydrobromination zone is rapidly chilled as it leaves the dehydrobromination zone to prevent or at least suppress the extent to which the ar-bromostyrene product is polymerized thermally.

19. A process of claim 12 wherein:
(a) the 2-bromoethyl-ar-bromobenzene fed to the dehydrobromination zone is predominantly 2-bromoethyl-ar-dibromobenzene;
(b) the temperature of the dehydrobromination zone is maintained at about 500° C.;
(c) the residence time in the dehydrobromination zone is 2 seconds or less;
(d) the dehydrobromination reaction is conducted in the vapor phase in a packed column containing glass beads or other solid inert packing material;
(e) the carrier gas is predominantly nitrogen; and
(f) the amount of water fed into the dehydrobromination zone corresponds to at least about 15 mols of water per mol of component (a).

20. A process of claim 19 wherein the effluent from the dehydrobromination zone is rapidly chilled as it leaves the dehydrobromination zone to prevent or at least suppress the extent to which the ar-bromostyrene product is polymerized thermally.

* * * * *